(12) United States Patent
Murthy et al.

(10) Patent No.: US 11,161,821 B2
(45) Date of Patent: Nov. 2, 2021

(54) PROCESS FOR THE PREPARATION OF ELTROMBOPAG OLAMINE AND ITS INTERMEDIATES

(71) Applicant: Aurobindo Pharma Ltd., Hyderabad (IN)

(72) Inventors: Moturu Venkata Ramakrishna Murthy, Hyderabad (IN); Tiwari Shashi Kant, Hyderabad (IN); Nadakudity Sailendra Kumar, Hyderabad (IN); Samala Bhanuchander, Hyderabad (IN); Rajesh Chennuri, Hyderabad (IN); Srinivasa Chary Katuroju, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 15/733,804

(22) PCT Filed: May 16, 2019

(86) PCT No.: PCT/IB2019/054050
§ 371 (c)(1),
(2) Date: Nov. 30, 2020

(87) PCT Pub. No.: WO2019/229572
PCT Pub. Date: Dec. 5, 2019

(65) Prior Publication Data
US 2021/0230120 A1    Jul. 29, 2021

(30) Foreign Application Priority Data
Jun. 1, 2018    (IN) .............................. 201841020662

(51) Int. Cl.
*C07D 231/48*    (2006.01)
(52) U.S. Cl.
CPC ................. *C07D 231/48* (2013.01)

(58) Field of Classification Search
CPC .................................................. C07D 231/48
See application file for complete search history.

(56) References Cited

U.S. PATENT DOCUMENTS 8,372,822 B2 *    2/2013    Leksic ................ C07D 231/46
514/150

* cited by examiner

*Primary Examiner* — Kamal A Saeed
(74) *Attorney, Agent, or Firm* — Jay R. Akhave; PatentScience LLC

(57) ABSTRACT

The present invention relates to an improved process for the purification of Eltrombopag olamine of compound of formula (2). The present invention also relates to an improved process for the preparation of Eltrombopag olamine intermediates and further conversion to Eltrombopag olamine of a compound of formula (2).

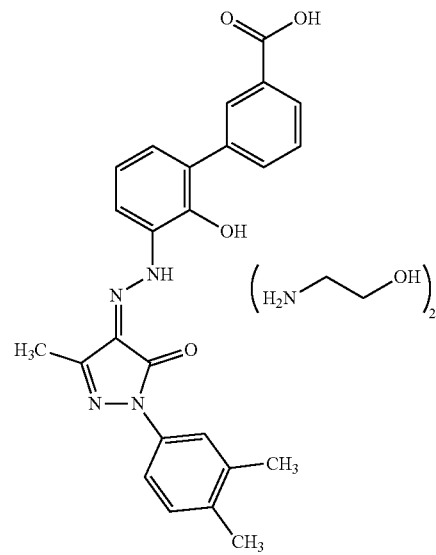

Formula 2

4 Claims, No Drawings

PROCESS FOR THE PREPARATION OF ELTROMBOPAG OLAMINE AND ITS INTERMEDIATES

FIELD OF THE INVENTION

The present invention relates to a process for the purification of Eltrombopag olamine. In one aspect, the present invention also relates to an improved process for the preparation of Eltrombopag olamine and its intermediates.

BACKGROUND OF THE INVENTION

Eltrombopag is chemically known as 3'-{(2Z)-2-[1(3,4-dimethylphenyl)-3-methyl-5-oxo-1,5-dihydro-4H-pyrazol-4-ylidene]hydrazino}-2'-hydroxy-3-biphenylcarboxylic acid, as shown below a Compound of Formula (1). Eltrombopag approved as bisethanolamine or olamine salt as shown below a Compound of Formula (2). Eltrombopag olamine is a biphenyl hydrazone. Eltrombopag olamine is marketed under the brand name PROMACTA®. PROMACTA (Eltrombopag) tablets contain Eltrombopag olamine, a small molecule Thrombopoeitin (TPO) receptor agonist for oral administration. Eltrombopag interacts with the transmembrane domain of the TPO receptor (also known as cMpl) leading to increased platelet production.

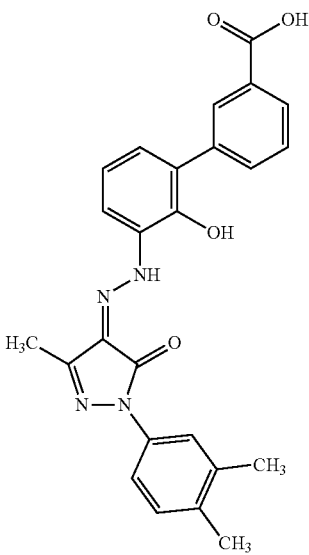

Formula 1

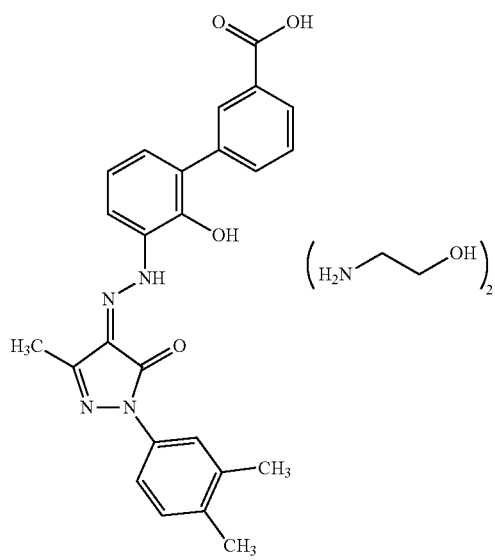

Formula 2

FDA approved Promacta® (Eltrombopag) Tablets for the treatment of thrombocytopenia in patients with chronic immune (idiopathic) thrombocytopenic purpura (ITP) who have had an insufficient response to corticosteroids, immunoglobulins or splenectomy. FDA also approved, Promacta® (Eltrombopag) for Oral Suspension and for the treatment of thrombocytopenia in adult and pediatric patients one year and older with chronic immune (idiopathic) thrombocytopenia (ITP) who have had an insufficient response to corticosteroids, immunoglobulins or splenectomy.

Eltrombopag (1) along with pharmaceutically acceptable salts, hydrates, solvates and esters thereof, disclosed first time in U.S. Pat. No. 7,160,870, which is hereby incorporated by reference. US '870 patent discloses 2-bromo-6-nitrophenol is protected by reaction with an alkylating agent such as benzyl bromide or preferably methyl iodide in the presence of a base such as sodium hydride or potassium carbonate in a suitable solvent such as dimethylformamide, tetrahydrofuran or acetone to give protected nitrophenol (Prot=alkyl or substituted alkyl, e.g. methyl, benzyl). Coupling of this compound with 3-carboxyphenylboronic acid, in the presence of a catalyst tetrakistriphenylphosphino palladium and a base such as sodium carbonate to triethylamine in a suitable solvent such as aqueous 1,4-dioxane or dimethylformamide afforded substituted aryl compound. Removal of the protecting group (Prot) is accomplished using a protic or Lewis acid; such as concentrated hydrobromic acid, boron tribromide or trimethylsilyl iodide to afford the phenol compound. Reduction of the nitro group by catalytic hydrogenation or mediated by a reducing metal such as iron of tin dichloride in a suitable solvent such as ethanol, acetic acid; or water gives the 3'-Amino-2'-hydroxy-1,1'-biphenyl-3-carboxylic acid (Amine Compound) of a Compound of Formula (A), which is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to Eltrombopag in a coupling reaction with 2-(3,4-dimethylphenyl)-5-methyl-1H-pyrazol-3(2H)-one (Pyrazolone Compound) of a Compound of Formula (B) in the presence of a base, preferably sodium hydrogen carbonate, or an acid, preferably hydrochloric acid.

The Process as Shown in Scheme-I Below:

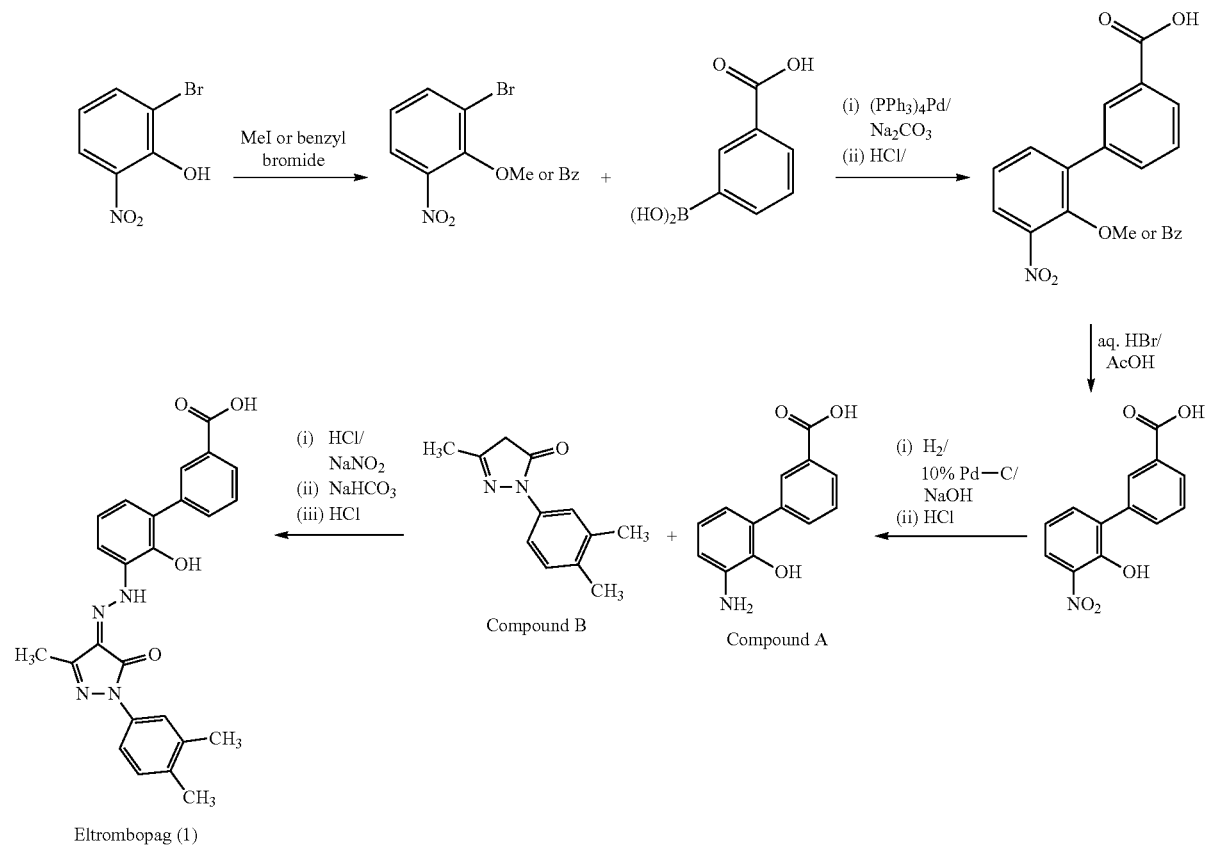

Scheme-I

The free acid is poorly soluble in water (approximately 5 micrograms per milliliter). This poor solubility adversely affects the ability of the free acid to be formulated into pharmaceutical dosage forms and reduces the bioavailability of the compound in vivo. The processes disclosed in the literature involve several chemical steps and provide the product in a very low overall yield. The given processes involve use of methyl iodide which is expensive and exhibits moderate to high acute toxicity for inhalation and ingestion and result into an expensive process for the preparation of the intermediate and the final Eltrombopag API. The given Benzyl bromide is lachrymatory compound and expensive in comparison to other compounds. Due to its lachrymatory property commercial use of it is less preferred.

U.S. Pat. No. 7,547,719 reported Eltrombopag olamine (bisethanolamine) salt (2) and process for the preparation thereof by treating Eltrombopag with two or more equivalents of ethanolamine and finally the suspension was filtered and the dark purple solid washed on the filter with Industrial Methylated Spirit (IMS).

The given process involves Eltrombopag olamine from Eltrombopag free acid. Therefore it is always advantageous to prepare Eltrombopag olamine without isolation of Eltrombopag. Direct preparation of Eltrombopag olamine from Eltrombopag free acid reduces one isolation and drying operation which helps in enhancing throughput of the product during commercialization.

U.S. Pat. No. 8,022,093 reported new polymorphs of Eltrombopag (1) and Eltrombopag olamine (bisethanolamine) salt (2) and process for the preparation thereof, by suspending Eltrombopag in ethanol and the reaction mixture treated with ethanolamine and the reaction mixture was refluxed and cooled to get Eltrombopag olamine. US '093 patent also discloses a process of crystalline Eltrombopag olamine, from amorphous Eltrombopag olamine was slurried with cumene solvent.

The given processes involve use of cumene is a class 2 solvent (ICH limit: 70 ppm) and therefore it's use should be avoided in final stage of API.

WO 2016035018 discloses a process of crystalline Eltrombopag olamine, by crystalline Eltrombopag was added to THF and then added ethanolamine in ethanol and finally washed with ethanol.

Following the above process, most of the time Eltrombopag fails in residual solvent content (THF content). THF gets trapped in molecule therefore it becomes difficult to remove it by drying operation.

IPCOM000212582D reported recrystallization of crude Eltrombopag olamine from a mixture of monoethanolamine and one or more solvents like ethanol.

The above process, yield is very less with crystallization using monoethanolamine.

EP 2865662 reported, 2-Bromo-6-nitrophenol is reacted with benzyl chloride using potassium carbonate and potassium iodide (KI) in acetone solvent to produce 2-(benzyloxy)-1-bromo-3-nitrobenzene.

The Process as Shown in Scheme-II Below:

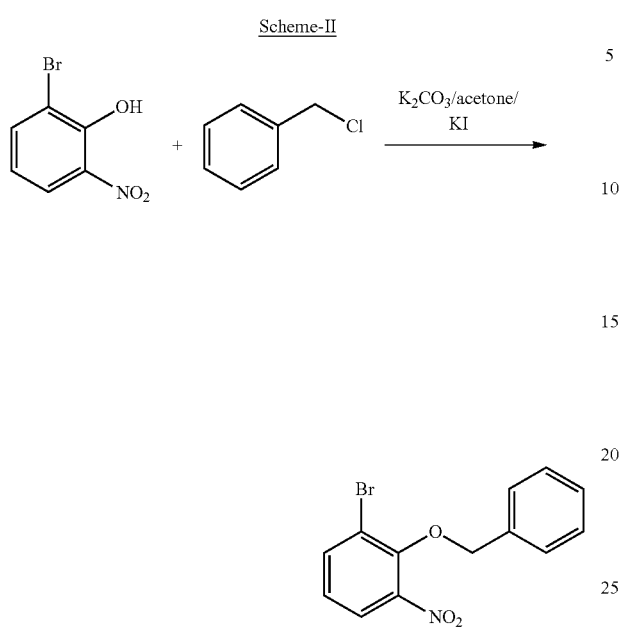

From the above process, it is observed that it requires more than 15 hours of time to complete the reaction; hence it is industrially not feasible.

Considering the importance of Eltrombopag olamine (2), there is always a need for an alternative preparative routes, which for example, involve fewer steps, use reagents that are less expensive and/or easier to handle, consume smaller amounts of reagents, provide a higher yield of product, have smaller and/or more eco-friendly waste products, and/or provide a product of higher purity.

Moreover the prior art processes do not disclose preparation of pure Eltrombopag olamine, substantially free from impurities. The removal of the impurities form the final API is very essential as the compound is known to have impurities.

In view of this, our scientists have developed the present invention; it has now surprisingly been found that the pure Eltrombopag olamine have numerous advantages over the reported processes.

OBJECTIVE OF THE INVENTION

The main objective of the present invention is a process for the purification of Eltrombopag olamine with high purity and good yield on commercial scale and an improved process for the preparation of Eltrombopag olamine and its intermediates.

SUMMARY OF THE INVENTION

In one embodiment, the present invention provides a process for the purification of Eltrombopag olamine salt of a Compound of Formula (2):

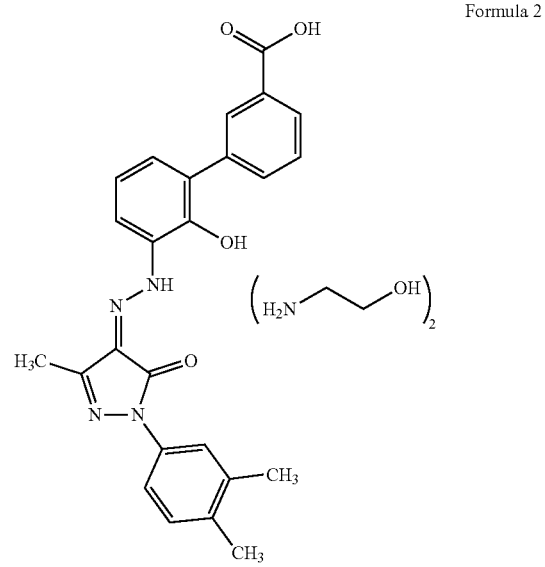

which comprises:
(i) providing a solution of Eltrombopag olamine salt of a Compound of Formula (2) in a suitable solvent;
(ii) optionally, filtering the resulting solution;
(iii) adding an anti-solvent to the resulting solution; and
(iv) isolating the pure Eltrombopag olamine salt of a Compound of Formula (2).

In another embodiment, the present invention provides a process for the purification of Eltrombopag olamine salt of a Compound of Formula (2): which comprises:
(i) providing a solution of Eltrombopag olamine salt of a Compound of Formula (2) in Dimethyl sulfoxide (DMSO) solvent;
(ii) optionally, filtering the resulting solution;
(iii) adding ethanol as an anti-solvent to the resulting solution; and
(iv) isolating the pure Eltrombopag olamine salt of a Compound of Formula (2).

In another embodiment, the present invention provides an improved process for the preparation of a Compound of Formula (C):

wherein R is a protecting group comprises substituted or unsubstituted alkyl or aryl group and X is a halogen;

which comprises the step of reacting a Compound of Formula (D);

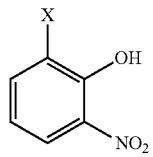

Formula D with a Compound of formula (E);

RxX    Formula E wherein R is a protecting group comprises substituted or unsubstituted alkyl or aryl or aralkyl group and X is a halogen;

in the presence of a phase transfer catalyst to produce a Compound of Formula (C).

In another embodiment, the present invention provides an improved process for the preparation of 2-(benzyloxy)-1-bromo-3-nitrobenzene of a Compound of Formula (F):

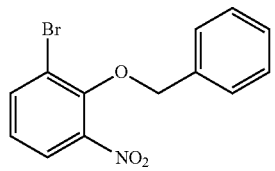

Formula F which comprises the step of reacting 2-Bromo-6-nitrophenol of a Compound of Formula (G);

Formula G with benzyl chloride of a Compound of formula (H)

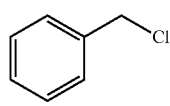

Formula H in the presence of a phase transfer catalyst to produce a Compound of Formula (F); and optionally further converted to Eltrombopag or Eltrombopag olamine salt.

DETAILED DESCRIPTION OF THE INVENTION

In one embodiment, the present invention provides a process for the purification of Eltrombopag olamine salt of a Compound of Formula (2):

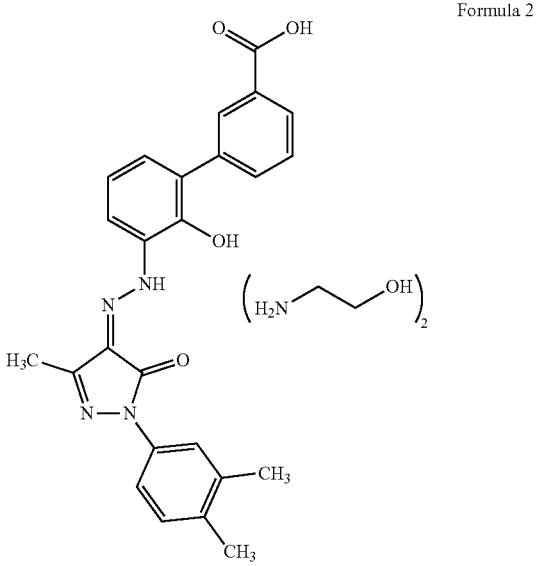

Formula 2 which comprises:
(i) providing a solution of Eltrombopag olamine salt of a Compound of Formula (2) in a suitable solvent;
(ii) optionally, filtering the resulting solution;
(iii) adding an anti-solvent to the resulting solution; and
(iv) isolating the pure Eltrombopag olamine salt of a Compound of Formula (2).

In still another embodiment, suitable solvent used in step (i) is selected from but not limited to dimethyl sulfoxide (DMSO), N,N- dimethylacetamide, N-methyl-pyrrolidine, tetrahydrofuran, or N,N- dimethylformamide and/or mixtures thereof.

In still another embodiment, anti solvent used in step (ii) is selected from but not limited to ethanol, methanol, ethyl acetate, isopropyl alcohol, n-butanol, petroleum ether, diisopropyl ether, methyl tert-butyl ether, diethyl ether and/or mixtures thereof.

In still another embodiment, after adding suitable solvent in step (i) heating the reaction mixture to 50-70° C., preferable 65-70° C. and further stirred the reaction mixture up to 30 minutes, preferable 20 minutes. Filtering the resulting solution through micron filter and cooled to 40-45° C.

In still another embodiment, after adding anti-solvent in step (ii) stirred the reaction mixture up to 1-2 hours, preferably 1 hour and cooled to 20-30° C.

In still another embodiment, isolation of the resulting pure Eltrombopag olamine salt of a Compound of Formula (2) may involve methods such as removal of solvent by filtration, distillation under vacuum or removal of solvent under reduced pressure.

In another embodiment, the present invention provides Eltrombopag olamine Salt obtained is in crystalline form.

In another embodiment, the present invention provides a process for the purification of Eltrombopag olamine salt of a Compound of Formula (2): which comprises:
(i) providing a solution of Eltrombopag olamine salt of a Compound of Formula (2) in a Dimethyl sulfoxide (DMSO) solvent;
(ii) optionally, filtering the resulting solution;
(iii) adding ethanol as an anti-solvent to the resulting solution; and
(iv) isolating the pure Eltrombopag olamine salt of a Compound of Formula (2).

In still another embodiment, after adding Dimethyl sulfoxide (DMSO) solvent in step (i) heating the reaction mixture to 50-70° C., preferable 65-70° C. and further stirred the reaction mixture up to 30 minutes, preferable 20 minutes. Filtering the reaction mixture and cooled to 40-45° C.

In still another embodiment, after adding ethanol in step (ii) stirred the reaction mixture up to 1-2 hours, preferable 1 hour and cooled to 20-30° C.

In still another embodiment, isolation of the resulting pure Eltrombopag olamine salt of a Compound of Formula (2) may involve methods such as removal of solvent by filtration, distillation under vacuum or removal of solvent under reduced pressure.

In another embodiment, the present invention provides an improved process for the preparation of a Compound of Formula (C):

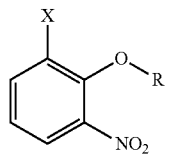

Formula C wherein R is a protecting group comprises substituted or unsubstituted alkyl or aryl group and X is a halogen; which comprises the step of reacting a Compound of Formula (D);

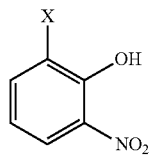

Formula D with a Compound of formula (E);

R—x  Formula E wherein R is a protecting group comprises substituted or unsubstituted alkyl or aryl group and X is a halogen;
in the presence of a phase transfer catalyst to produce a Compound of Formula (C).

In still another embodiment, the phase transfer catalyst comprises, quaternary ammonium salts are selected from but not limited to tetrabutylammonium iodide, tetrabutylammonium bromide, benzyltriethylammonium chloride, methyltricaprylammonium chloride, methyltributylammonium chloride, and methyltrioctylammonium chloride, hexadecyltributylphosphonium bromide; crown ethers and/or mixtures thereof.

In still another embodiment, preferably the phase transfer catalyst is tetrabutylammonium iodide.

In still another embodiment, the above reaction is carried out in the presence of a base and a solvent.

The base is organic or inorganic base. The inorganic base comprises potassium carbonate, lithium carbonate, sodium carbonate, sodium ethoxide, sodium bicarbonate, potassium bicarbonate, and mixtures thereof. The organic base comprises alkali metal acetate such as potassium acetate, sodium acetate; diisopropylamine, diisopropylethylamine triethylamine, dimethylamine, trimethyl amine, pyridine, 1,8-diazabicyclo[5.4.0]undec-7-ene (DBU), and mixtures thereof.

In still another embodiment, the solvent used in the reaction step comprises polar protic solvent or polar aprotic solvent or non-polar solvent and/or mixtures thereof.

The polar protic solvent comprises water, methanol, ethanol, isopropyl alcohol, n-butanol, and/or mixtures thereof; polar aprotic solvent comprises dimethylformamide (DMF), dimethylsulfoxide (DMSO), tetrahydrofuran (THF), acetonitrile, acetone, ethyl acetate, N-methylpyrrolidone- and/or mixtures thereof; and non-polar solvents comprises hexane, benzene, toluene, 1,4-dioxane, chloroform, diethyl ether, methylene chloride (CH2C12) and/or mixtures thereof.

In one more embodiment, the reaction is carried out at reflux temperature depending upon the solvent used in the reaction for a time period of 2-5 hours.

In still another embodiment, after completion of the reaction heating the reaction mixture to 80-100° C., and further cooled to 40-45° C. and added water and cyclohexane for isolation.

In still another embodiment, the present invention provides an improved process for the preparation of 2-(benzyloxy)-1-bromo-3-nitrobenzene of a Compound of Formula (F):

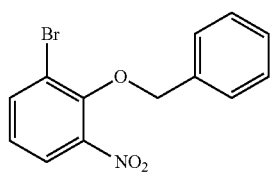

Formula F which comprises the step of reacting 2-Bromo-6-nitrophenol of a Compound of Formula (G);

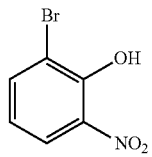

Formula G with benzyl chloride of a Compound of formula (H)

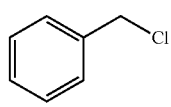

Formula H in the presence of a phase transfer catalyst to produce a Compound of Formula (F); and optionally further converted to Eltrombopag or Eltrombopag olamine salt.

In still another embodiment, the phase transfer catalyst as mentioned above.

In still another embodiment, preferably the phase transfer catalyst is tetrabutylammonium iodide.

In still another embodiment, the above reaction is carried out in the presence of a base and a solvent.

In still another embodiment, base and solvent are as mentioned above.

In still another embodiment, preferably the base is potassium carbonate.

In still another embodiment, preferably the solvent is acetonitrile.

In one more embodiment, the reaction is carried out at reflux temperature depending upon the solvent used in the reaction for a time period of 2-5 hours.

In still another embodiment, after completion of the reaction heating the reaction mixture to 80-90° C., and further cooled to 40-45° C. and added water and cyclohexane for isolation.

In another embodiment, the present invention provides an improved process for the preparation of Eltrombopag olamine salt of a Compound of Formula (2); which comprises;

(a) reacting 2-Bromo-6-nitrophenol of a Compound of Formula (G);

Formula G with benzyl chloride of a Compound of formula (H)

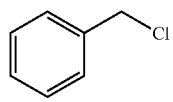

Formula H in the presence of a phase transfer catalyst to produce 2-(benzyloxy)-1-bromo-3-nitrobenzene of a Compound of Formula (F);

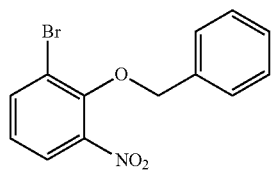

Formula F (b) reacting a Compound of Formula (F) with 3-boronobenzoic acid of a Compound of Formula (I);

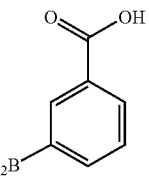

Formula I to produce 2'-(benzyloxy)-3'-nitro-1,1'-biphenyl-3-carboxylic acid of a Compound of Formula (J);

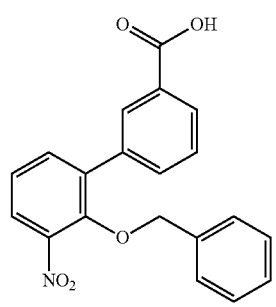

Formula J (c) hydrogenating a Compound of Formula (J) to produce a Compound of Formula (A);
(d) reacting a Compound of Formula (A) with a Compound of Formula (B) to produce Eltrombopag of a Compound of Formula (1);
(e) treating Eltrombopag of a Compound of Formula (1) with or without isolation with ethanolamine to produce Eltrombopag olamine salt of a Compound of Formula (2):
(f) optionally purifying Eltrombopag olamine salt of a Compound of Formula (2).

In another embodiment, in step (a) phase transfer catalyst is as mentioned above.

In another embodiment, step (a) is carried out in the presence of a base and a solvent, which are as mentioned above.

In another embodiment, step (b) is carried out, in the presence of a catalyst, preferably 10% palladium on carbon and a base such as sodium carbonate in a suitable solvent such as aqueous methanol followed by acidified with dilute hydrochloric acid to adjust pH 4-5.

In another embodiment, hydrogenation and removal of protecting group step (c) is accomplished by catalytic hydrogenation using 10% palladium on carbon in a suitable solvent such as methanol or water, followed by acidified with aq. hydrochloric acid to adjust pH 0.5-1 at 25-30° C. Thereafter adjust pH to 4.5-5° by adding 10% aqueous sodium hydroxide to gives Amine Compound of a Formula (A).

In another embodiment, in step (d) Amine Compound of a Formula (A) is diazotized by reaction with aq. sodium nitrite and an appropriate acid, such as nitric acid, sulfuric acid or, preferably, hydrochloric acid, in an appropriate aqueous solvent, such as methanol-water mixture to produce a diazonium species, aqueous solution of sulfamic acid was added, which is directly converted to Eltrombopag in a coupling reaction with 2-(3,4-dimethylphenyl)-5-methyl-1H-pyrazol-3(2H)-one (Pyrazolone Compound) of a Compound of Formula (B), which in-situ further converted to Eltrombopag olamine salt of a Compound of Formula (2) by treatment with ethanolamine in step (e).

The present invention of an improved process for the preparation of Eltrombopag of a Compound of Formula (1) and its intermediates can be used for the preparation of Eltrombopag pharmaceutical acceptable salts thereof.

In another embodiment, in step (f) purification of Eltrombopag olamine salt of a Compound of Formula (2) by conventional methods.

In another embodiment, purification is carried out by crystallization using a solvent and anti-solvent system.

In another embodiment, in step (f) solvent and anti-solvent are mentioned above.

In another embodiment, the present invention provides Eltrombopag olamine Salt obtained is in crystalline form.

The state of such crystalline form can be investigated using known analytical methods, e.g. by Powder X-Ray Diffraction (PXRD) Methods or by Differential Scanning Calorimetry (DSC) or by Infrared (IR) spectroscopy.

As used herein, the term "reduced pressure" refers to a pressure below 50 mmHg.

Drying may be suitably carried out in a tray dryer, vacuum oven, Buchi® Rotavapor®, air oven, fluidized bed dryer, spin flash dryer, flash dryer, cone dryer, agitated nutsche filter cum dryer, nauta dryer or the like or any other suitable dryer. The drying may be carried out at temperature of less than 100° C., or less than about 70° C., or any other suitable temperature. The drying may be carried out under reduced pressure, that is, less than standard atmospheric pressure or at atmospheric pressure or any other suitable pressure. The drying may take place over a period of about 30 minutes to about 12 hours, or any other suitable time period.

The following examples illustrate the nature of the invention and are provided for illustrative purposes only and should not be construed to limit the scope of the invention.

EXAMPLES

Example 1: Preparation of 2-(benzyloxy)-1-bromo-3-nitrobenzene [Benzyl Protected Bromonitrophenol]

In a 2 L round bottom flask, anhydrous potassium carbonate (76 g), tetrabutylammonium iodide (5 g) and benzyl chloride (61 g) were added at 25-35° C. to a stirred solution of 2-bromo-6-nitrophenol (100 g) in acetonitrile (1000 mL) at 25-30° C. The resulting suspension was refluxed at 80±2° C. for ~3 h. After completion of reaction (HPLC monitored), the reaction mass was concentrated at atmospheric pressure at 80-90° C. Thereafter, concentrated mass was cooled at 40-50° C. and water (1600 mL) and cyclohexane (600 mL) were added. The Reaction mass was stirred at 50-60° C. for ~30 minutes. The layers were separated. Organic layer was washed with 200 mL of water at 50-60° C. The obtained organic layer was cooled to 25-30° C. and stirred for ~30 minutes then further cooled to 12-18° C. and continued stirring at this temperature for another ~2 h to complete the precipitation of the product. Product was filtered and washed with pre-cooled cyclohexane (100 mL). The obtained wet product was dried at 40-45° C. under reduced pressure (~50 mm Hg) for 10 h to furnish 123.0 g (87% yield) as an off white powder with >99% purity, by HPLC.

$^1$H NMR (500 MHz, CDCl$_3$) 7.83(dd, J=1.5 Hz & 6.5 Hz, 1H), 7.77(dd, J=1.5 Hz & 8.5 Hz, 1H), 7.54(d, J=7.0 Hz, 2H), 7.44-7.36(m, 3H), 7.15(t, J=8.5 Hz, 1H), 5.25(s, 2H)

Example 2: Preparation of 2'-(Benzyloxy)-3'-Nitro-1,1'-Biphenyl-3-Carboxylic Acid [Benzyl Protected Biphenyl Nitro Compound]

In a round bottom flask, sequentially 3-boronobenzoic acid (129.4 g), 10% Palladium on carbon (10 g) and sodium carbonate (206.5 g) was added to a stirring suspension of 2-(benzyloxy)-1-bromo-3-nitrobenzene (200 g) in aqueous methanol (2 Lt; 1:1 ratio) at 25-35° C. The resulting reaction mass was heated to 70-80° C. and stirred at this temperature for ~3 h. After completion of reaction (HPLC monitored), the reaction mass was cooled to 25-30° C. and filtered through hyflo pad to remove palladium. The reaction mass was filtrated and acidified with dilute hydrochloric acid (~530 g) to pH 4-5 (product starts precipitating out). Thus, the obtained slurry was stirred for ~1 h at 25-30° C. to complete precipitation of the product. Product was filtered under suction and washed with an aqueous methanol solution (200 mL; 1:1 ratio). Wet product was dried at 40-50° C. under vacuum (~50 mm Hg) for 10 h to obtain 206 g (90.7% yield) of white to light brown colored powder with >98% purity, by HPLC.

Example 3: Preparation of 3'-amino-2'-hydroxy-1,1'-Biphenyl-3-Carboxylic Acid [Biphenyl Amino Compound (A)]

In a 5 Lt. autoclave 2'-(benzyloxy)-3'-nitro-1,1'-biphenyl-3-carboxylic acid (200 g) and methanol were charged (4 Lt.) at 25-30° C. 10% w/w Palladium on carbon was added (10 g) to the suspension under nitrogen atmosphere while stirring. Autoclave was evacuated with nitrogen followed by hydrogen and applied hydrogen pressure. Reaction mass was hydrogenated at 25-30° C. by maintaining the hydrogen pressure at 70-80 psi for ~4 h. Thereafter, hydrogen in autoclave was replaced with nitrogen and mass filtered through hyflo bed to remove catalyst. The contents were stirred, filtered and concentrated at below 40° C. under reduced pressure to get solid residue. This solid residue was suspended in water (4 Lt.) at 25-30° C. and acidified with 6 N of aq. hydrochloric acid (~200 mL) to the pH 0.5-1.0 at 25-30° C. Thus, obtained solution was filtered to remove any un-dissolved material and filtrate was washed with ethyl acetate (2×200 mL). Thereafter, adjusted the pH of the aqueous layer to 4.5-5 by adding 10% aqueous solution of sodium hydroxide (~480 mL) at 25-30° C. Product precipitated out, which was further stirred for ~30 minutes and filtered at 25-30° C. Obtained wet solid was dried at 45-50° C. under vacuum (~50 mm Hg) for 8-10 h to get product as a brown powder (118 g; 90% yield) with >98% HPLC purity.

Example 4: Preparation of Eltrombopag Olamine

In a round bottom flask, dilute hydrochloric acid (~270 mL, prepared by mixing 114 g of ~35% w/w hydrochloric acid and 156 g of water) was added to a pre-cooled (0-5° C.) suspension of biphenyl amino compound (A) (100 g; 0.44 mole) in 2.5 Lt of methanol slowly by maintaining temperature of the reaction mass at 0-5° C. Solution of sodium nitrite (~120 mL, prepared by dissolving 33.15 g; 0.48 mole, of sodium nitrite in 100 mL of water) was added to the reaction mass at 0-5° C. Reaction mass was stirred at 0-5° C. for 1 h to complete diazotization. Then aqueous solution of sulfamic acid (~105 mL, prepared by dissolving 8.5 g; 0.9 mole, in 100 mL of water) was added at 0-5° C. to the mass and stirred at this temperature for another 1 h.

2'-(3,4-Dimethylphenyl)-5-methyl-(1H)-pyrazole-3-(2H)-one (Compound B) (88.2 g; 0.44 mole) was added to the resulting reaction mass, in one portion at 0-5° C. and then the temperature of reaction mixture was allowed to 20-30° C. Thereafter, monoethanolamine (133 g) was added to the reaction mass at 25-30° C. (pH=8.5-9.5) and further stirred for 2 h, solid product precipitated out. The product was filtered under suction, washed the solid with mixture of methanol:water (~100 mL; 1:1 ratio) and dried at 65-70° C. under vacuum (~50 mmHg) for 10 h to get Eltrombopag olamine crude (226 g; 92% yield) with >99% purity.

Example 5: Purification of Eltrombopag Olamine

In a round bottom flask, Eltrombopag olamine, crude (200 g) was dissolved in DMSO (1 Lt) at 65-70° C. and stirred for ~20 minutes at this temperature. Thus the obtained solution was filtered through micron filter at 40-45° C. and washed with 400 mL of DMSO at 40-45° C. Ethanol (3 Lt) was added to the obtained solution, and reaction mass was stirred for ~1h at 40-45° C. Then reaction mass was slowly cooled to 25-30° C. and stirred at this temperature for ~12 h to complete precipitation of product. Thereafter, product was filtered and washed with 400 mL of ethanol at 25-30° C. Wet product was dried at 65-70° C. under reduced pressure (~50 mm Hg) to obtain 152 g (76% yield) as a brick red colored crystalline powder with >99.9% purity.

We claim:
1. A process for the purification of Eltrombopag olamine salt of a Compound of Formula (2);

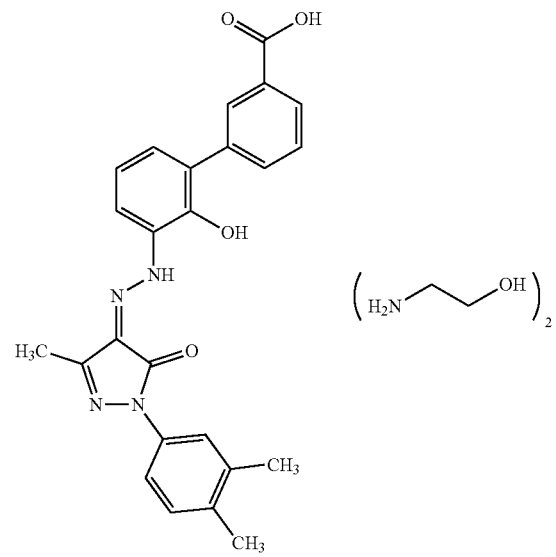

Formula 2 which process comprises the steps of:
(i) providing a solution of Eltrombopag olamine salt of a Compound of Formula (2) in a suitable solvent;
(ii) optionally, filtering the resulting solution;
(iii) adding an anti-solvent to the resulting solution; and
(iv) isolating the pure Eltrombopag olamine salt of a Compound of Formula (2).

2. The process according to claim 1, suitable solvent used in step (i) is selected from dimethyl sulfoxide (DMSO), N,N- dimethylacetamide, N-methyl-pyrrolidine, tetrahydrofuran, or N,N- dimethylformamide and/or mixtures thereof.

3. The process according to claim 1, anti-solvent used in step (ii) is selected from ethanol, methanol, ethyl acetate, isopropyl alcohol, n-butanol, petroleum ether, diisopropyl ether, methyl tert-butyl ether, diethyl ether and/or mixtures thereof.

4. A process for the purification of Eltrombopag olamine salt of a Compound of Formula (2): which comprises:
(i) providing a solution of Eltrombopag olamine salt of a Compound of Formula (2) in Dimethyl sulfoxide (DMSO) solvent;
(ii) optionally, filtering the resulting solution;
(iii) adding ethanol as an anti-solvent to the resulting solution; and
(iv) isolating the pure Eltrombopag olamine salt of a Compound of Formula (2).

* * * * *